United States Patent [19]
Selden et al.

[11] Patent Number: 6,018,097
[45] Date of Patent: Jan. 25, 2000

[54] TRANSGENIC MICE EXPRESSING HUMAN INSULIN

[75] Inventors: Richard Selden, Camb.; Howard Goodman, Newton, both of Mass.

[73] Assignee: The General Hospital Corporation, Boston, Mass.

[21] Appl. No.: 08/419,850

[22] Filed: Apr. 11, 1995

Related U.S. Application Data

[63] Continuation of application No. 08/228,455, Apr. 15, 1994, abandoned, which is a continuation of application No. 07/840,635, Feb. 21, 1992, abandoned, which is a continuation of application No. 07/430,934, Nov. 2, 1989, abandoned, which is a continuation of application No. 06/865,120, May 20, 1986, abandoned.

[51] Int. Cl.[7] .................. A01K 67/00; A01K 67/033; C12N 15/00; G01N 33/00
[52] U.S. Cl. ................... 800/18; 800/3; 800/14; 800/25
[58] Field of Search ................... 800/2, DIG. 1; 435/172.3; 424/2, 9; 935/111

[56] References Cited

U.S. PATENT DOCUMENTS

| | | | |
|---|---|---|---|
| 4,431,740 | 2/1984 | Bell et al. | 435/253 |
| 4,564,517 | 1/1986 | Fudenberg et al. | 424/9 |
| 4,736,866 | 4/1988 | Leder et al. | 800/2 |
| 4,870,009 | 9/1989 | Evans et al. | 435/70 |
| 4,873,191 | 10/1989 | Wagner et al. | 435/172.3 |

FOREIGN PATENT DOCUMENTS

| | | |
|---|---|---|
| 0 169 672 | 1/1986 | European Pat. Off. ........ C12N 15/00 |
| WO 82/04443 | 6/1981 | WIPO . |
| WO 83/00164 | 6/1981 | WIPO . |
| 8200780 | 6/1982 | WIPO . |

OTHER PUBLICATIONS

Palmiter et al Cell 41, 343–345 (1985).
Stewart, T.A., et al., "Human β–Globin Gene Sequences Injected into Mouse Eggs, Retained in Adults, and Transmitted to Progeny, " *Science* 217:1046–1048 (1982).
Constantini, F., and Lacy, E., "Introduction of rabbitt β–globin Gene into the Mouse Germ Line," *Nature*294:92–94 (1981).
Katsuki, M., et al., "Experimental System with Transgenic Mouse" *Protein, Nucleic Acid* , Enzymes 40:2001–2007 (1995).
Palmiter, et al., "Differential Regulation of Metallothionein Thymidine Kinase Fusion Genes in Transgeric Mice and Their Offspring," *Cell*29:701–710 (1982).
Bucchini et al., *Proc. Natl. Acad. Sci. USA* 83: 2511–2515 (Apr. 1986).
Jami et al. *Journal of In Vitro Fertilization and Embryo Transfer* (1986), Biological Abstracts Reference No. 31074293.
Jami et al., *J. In. Vitro Fert. Embryo Transfer* 3:70 (1986).
Selden et al., *Nature* 321:525–528 (1986).

Brinster, Ralph L and Palmiter, Richard D., "Introduction of Genes into the Germ Line of Animals," *Friends of the Harvey Society* , 1–38 (1984–1985).
Brinster, Ralph L and Palmiter, Richard D., "Germ–Line Transformation of Mice," *Ann. Rev. Genet.* 20:465–99 (1986).
McDonald, Raymond J. et al. "Transgenic Progeny Inherit Tissue–Specific Expression of Rat Elastase I Genes," *DNA* vol. 5 5:393–401 (1986).
Hammer, Robert E. et al., "Estrogen Regulation of the Avian Transferrin Gene in Transgenic Mice," *Molecular and Cellular Biology* , vol. 6: (4)1010–1014 (1986).
Hammer, Robert E. et al., "Genetic Engineering of Mammalian Embryos[1,2,3] ," *J. Anim. Sci.* 63:269–278 (1986).
Pursel, V.G. et al., "Progress on Gene Transfer in Farm Animals," *Veterinary Immunology and Immunopathology,* 17:303–312 (1987).
Hammer, Robert E. et al., "Genetic Engineering of Livestock," vol. 244:1281–2257 (1989).
Allison, Janette et al., "Tissue–Specific and Hormonal Regulation of the Gene for Rat Prostatic Steroid–Binding Protein in Transgenic Mice," *Molecular and Cellular Biology,* vol. 9(5) :2254–2257 (1989).
Murphy, Carol et al., Regulation of the Human C–reactive Gene in Transgenic Mice, The Journal of Biological Chemistry, Vol. 270 (4) :704–708 (1995).
Corcoran, Colm M. et al., "High–level Regulated Expression of the Human G6PD Gene in Transgenic Mice," *Gene,* 173:241–246 (1996).
Selden et al., "Glucocorticoid regulation of human hormone expression in transgenic mice", J. of Cell. Bio. vol. Suppl. No. 9B, P. 204 (1985) abstract 0943.
Bucchini et al., "Pancreatic expression of human insulin gene in transgenic mice", Proc. Natl. Acad. Sci. USA, 83:2511–2515 (1986).
Palmiter et al., Cell 41 : 343–345 (1985).
Townes et al., The EMBO Journal 4:1715–1723 (1985).
Stewart et al., Cell 38:627–637 (1984).
Gordon et al, Methods in Enzymology vol. 101 pp. 411–433.
Cappecchi, *Cell*, 22:479–488 (1980).

(List continued on next page.)

*Primary Examiner*—Deborah Crouch
*Attorney, Agent, or Firm*—Hamilton, Brook, Smith & Reynolds, P.C.

[57] ABSTRACT

A process for producing a transgenic mouse which contains and expresses the human insulin hormone gene. The insulin gene is expressed only in the pancreas of the transgenic mouse and is regulated by glucose, glucagon, or other insulin affectors in a manner which is indistinguishable from that of normal mice. Progeny of the trangenic mice inherit the human insulin gene in a Mendelian manner, with approximately 50% of the mice of each litter expressing the human insulin gene. The weights of the transgenic mice, growth rate, feeding behavior, reproductive capability, and longevity appear indistinguishable from normal mice. The mice are useful for studies of pharmacokinetics of insulin expression and for investigations of possible drug interactions with glucose homeostasis.

26 Claims, 3 Drawing Sheets

OTHER PUBLICATIONS

Gordon, et al., *Proc. Natl. Acad. Scie. USA*, 77:7380–7384 (1980).
Wagner, et al., *Proc. Natl. Acad. Sci. USA*, 78:6376–6380 (1981).
Grosschedl, et al., *Cell*, 38:647–658 (1984).
Brinster, et al., *Nature*, 306:332–336 (1983).
Palmiter, et al., *Nature*, 300:611–615 (1982).
Brinster, et al., *Cell*, 37:367–379 (1984).
Swift, et al., *Cell*, 38:639–646 (1984).
Lacy, et al., *Cell*, 34:343–358 (1983).
Hammer, et al., *Nature*, 311:65–67 (1984).
McKnight, et al., *Cell*, 34:335–341 (1983).
Palmiter, et al., *Cell*, 36:869–877 (1984).
Illmensee, et al., *Developemental Biology Using Purified Genes*, pp. 607–619 (1981).
Burki, et al., *The EMBO Journal*, 1:127–131 (1982).
Van Der Putten, et al., *Mol Gen Genet*, 198: 128–138 (1984).
Bell, et al. *Nature*, 284;26–32 (1980).
Hoppe, et al., *Biology of Reproduction*, 8:420–426 (1973).
Bucchini, et al., *Proc. Natl. Acad. Sci. USA*, 83:2511–2515 (1986).

TRANSGENIC MICE EXPRESSING HUMAN INSULIN

This application is a continuation of co-pending application Ser. No. 08/228,455 filed on Apr. 15, 1994, abandoned, which is a continuation of Ser. No. 07/840,635, filed Feb. 21, 1992, abandoned, which is a continuation of Ser. No. 07/430,934, filed Nov. 2, 1989, abandoned, which is a continuation of Ser. No. 06/865,120, filed May 20, 1986 abandoned. All of the above applications are incoporated herein by reference in their entirety.

FIELD OF THE INVENTION

The invention pertains to a process for producing a recombinant, transgenic mouse, capable of expressing the human insulin hormone. The invention further pertains to a mouse which expresses the human insulin hormone. The invention further pertains to a means of evaluating potential therapeutic agents in a transgenic human insulin-producing mouse which comprises introducing a potentially therapeutic agent into the transgenic mouse and monitoring the expression of human insulin production. The invention further pertains to the process of evaluating the effects of therapeutic agents on human proteins in transgenic animals.

BACKGROUND ART

The ability to incorporate specific genes into the genome of mammalian embryos has provided a useful in vivo system for the analysis of gene control and expression. The high efficiency transformation of cultured mammalian cells has been accomplished by direct microinjection of specific DNA sequences into the cell nucleus (Capecchi, M., *Cell* 22:479–488 (1980)). Gordon, J. W. et al. (*Proc. Natl. Acad. Sci. USA* 77:7380–7384 (1978)) demonstrated that DNA could be microinjected into mouse embryos, and found in the resultant offspring. Thus, at the present time, the ability to produce certain transgenic mice is well described and well known in the art.

The basic procedure used to produce transgenic mice requires the recovery of fertilized eggs from the oviducts of newly mated female mice. DNA which contains the gene desired to be transferred into the mouse is microinjected into the male pronucleus of each fertilized egg. Microinjected eggs are then implanted into the oviducts of one-day pseudopregnant foster mothers and carried to term (Wagner, T. E. et al., *Proc. Natl. Acad. Sci. USA* 78:6376–6380 (1981)). The newborn mice are then tested for the presence of the microinjected DNA by means known in the art and appropriate to detect the presence of the microinjected DNA.

Using essentially this procedure, Wagner, T. E. et al., successfully produced an adult mouse capable of expressing rabbit B-globin. This mouse was further capable of producing offspring which also expressed the rabbit B-globin gene. Additional cloned immunoglobulin genes have been introduced into mouse germ lines to produce transgenic mice which produce the cloned immunoglobulin. (Grosschedl, R. et al., *Cell* 38:647–658 (1984)), Brinster, R. L. et al., *Nature* 306: 332–336 (1983)). Palmiter, R. D. et al. (*Nature*, 300:611–615 (1982)) produced transgenic mice which carried the mouse metallothionein I promoter fused to the structural gene for rat growth hormone. These mice were found to produce elevated levels of rat growth hormone, and to exhibit dramatically enhanced growth. Brinster, R. L. et al., *Cell*, 37:367–379 (1984)) injected the SV40 early region genes and a metallothionein fusion gene into fertilized mouse eggs, using essentially the method described above. A high percentage of the transgenic mice which developed from these eggs developed tumors within the choroid plexus. SV40 T-antigen-mRNA and protein were readily detected in this affected tissue. However, SV40 T-antigen gene expression was barely detectable in unaffected tissues or in susceptible tissues prior to overt pathology, suggesting that tumorigenesis depended upon the activation of the SV40 genes. This work indicated that it was possible to microinject the genes which encode for a tumor virus into a mouse embryo and thereby produce a mouse with a predisposition to oncogenesis. Swift, G. M. et al. (*Cell*, 38:639–646 (1984)) produced a transgenic mouse which selectively expressed the gene for rat pancreatic elastase I at high levels in the mouse pancreas.

Cloned genes can be transferred into the mouse germ line by microinjection into the pronuclei of mouse zygotes. Such microinjected genes frequently integrate into chromosomes, are retained throughout development and are transmitted to offspring as Mendelian traits. (Grosschedl, R. et al.; Wagner, T. E. et al.). Investigators have reported that transgenic mice may be produced at an efficiency of between 10 and 30 percent using this procedure. Microinjected foreign genes have shown a tendency to be expressed in transgenic mice (Brinster, R. L. et al., Swift, G. M. et al.). Such expression, however, cannot be presumed. Lacy, E. et al., *Cell* 34:343–358 (1983) disclose a transgenic mouse containing the human B-globin gene that generally does not express this gene. Similarly, the rat and human growth hormone genes have been found to not be expressed under the control of their own promoters in transgenic mice which carry these genes (Wagner, T. E. et al.; Hammer, C. et al.). Expression of the chicken transferrin gene has been found to be enhanced only moderately in the liver (where it normally is preferentially expressed), relative to other tissues in a transgenic mouse which contains the chicken transferrin gene (McKnight, G. S. et al., *Cell* 34:335–341 (1983)). Thus, although the procedure for producing transgenic mice has been described in the art, the ability to produce specific transgenic mice which properly express the cloned gene remains imprecisely defined. It has been theorized that these aberrant results reflect the possibility that the cloned DNA has integrated into an essential region of the mouse chromosome that modifies its expression, or has undergone mutation or rearrangement in the process of integrating into the mouse chromosome.

Upon entry into the nucleus of the unicellular fertilized egg, the cloned gene fragments are believed to integrate at random sites on the mouse chromosomes. Once the cloned DNA has integrated into these sites it is, in general, stable and leads to the heritable transmission of these genes into progeny mice. Thus, the extremely variable expression of thymidine kinase in transgenic mice which carried the herpes simplex virus (type 1) gene is believed to result from a genetic rearrangement that occurred when the thymidine kinase fusion gene integrated into the mouse chromosome (Palmiter, R. D. et al., *Cell*, 36:869–877, (1984)).

The general method for producing transgenic mice is described in Wagner, T. E. et al., European Patent Application No. 81,570 (corresponding U.S. patent application No. 273,239) which specifically discloses a mouse expressing rabbit beta-globin gene in its erythrocytes.

Efforts to introduce the gene for human insulin into mice have been reported previously (Illmensee, K. et al., "Nuclear and Gene Transplantation in the Mouse." In: Brown B. D., Fox C. F., Eds. *Developmental Biology Using Purified Genes*, Academic Press, New York, pp 607–629 (1981); Burki, K. et al., Embo J. 1:127–131 (1982); Van der Putten, H. et al., *Mol. Gen. Genetic* 198:128–138 (1984)). These efforts resulted in the production of a mouse which contained the human insulin hormone gene sequences. The transgenic mouse produced by these laboratories was, however, unable to transmit the human insulin gene sequences to its progeny. Van der Putten, H. et al., showed that although progeny mice derived from a transgenic (insulin sequence bearing) mouse retained DNA sequences which had flanked the insulin gene sequence region, the progeny mice lacked all human insulin sequences. To explain how the insulin bearing sequences could have been deleted from the transgenic mice, while the flanking regions had been retained in these mice, Van der Putten, H. et al., postulated a germ line-specific excision event which specifically removed the human insulin sequences. Van der Putten, H. et al., concluded that the excision of the human insulin gene sequences might be a general phenomenon occurring during an initial step in the formation of the germ line in the transgenic female. The procedure employed by Van der Putten, H. et al. used a high number of circular DNA molecules containing the human insulin gene for the microinjections.

In conclusion, the prior art teaches the ability to produce certain transgenic mice which are capable of a tissue specific expression of a cloned gene. The prior art, however, also teaches the difficulty of specifically producing a transgenic mouse which expresses the human insulin gene. Although it has been possible to produce transgenic mice which carry DNA sequences of the gene for human insulin, these mice are not known to produce human insulin and have not been able to produce offspring which either express or carry the human insulin gene (Van der Putten H. et al., *Mol. Gen. Genetic* 198:128–138 (1984)).

It is therefore of great interest to develop a method for producing a mouse capable of expressing a human hormone or analogue of a human hormone and which can heritably transmit the capacity to express this hormone to its progeny mice.

SUMMARY OF THE INVENTION

A process is described for isolating a mouse which expresses human insulin. A cDNA fragment encoding a portion of human preproinsulin was used to probe a human gene library in bacteriophage lambda Charon 4a (described by R. M. Lawn, et al., *Cell* 15: 1157–1174 (1978)). By screening the recombinant phages by hybridization, for those containing human insulin gene sequences, a 12.5-kilobase EcoRI fragment was obtained. This fragment was sequenced and shown to contain the complete nucleotide sequence of the cloned human insulin gene (Bell, G. I. et al., *Nature* 284: 26–32 (1980)). The 12.5 kb EcoRI fragment was microinjected into the male pronucleus of a single-cell mouse embryo. The embryo was then transferred into a pseudo-pregnant foster mother for gestation. This procedure resulted in the birth of three viable mice containing human insulin gene sequences as detected by Southern hybridization analysis. One of these three mice, a male, was bred to generate a colony of several hundred offspring. The human insulin gene was transmitted in a Mendelian fashion, with approximately 50% of both the F1 and F2 offspring inheriting the injected DNA fragment.

In detail, the invention comprises:

A method for obtaining a target mouse whose cells contain a genetic sequence for all or part of the human prepropinsulin, proinsulin or insulin genes and which is capable of being bred to produce progeny mice whose cells contain the genetic sequences, comprising:

(a) isolating a fertilized egg from a first female mouse;
(b) transferring a genetic sequence which contains all or part of the human preproinsulin, proinsulin or insulin gene into the fertilized egg;
(c) transferring the fertilized egg containing the genetic sequence to the uterus of a pseudopregnant second female mouse;
(d) maintaining the second female mouse such that:
   (i) the second female mouse becomes pregnant with an embryo derived from the fertilized egg containing the genetic sequence,
   (ii) the embryo develops into the target mouse, and
   (iii) the target mouse is viably born from the second female mouse;
   wherein the target mouse contains a genetic sequence for human preproinsulin, proinsulin or insulin and is capable of being bred to produce progeny mice whose cells stably contain the genetic sequences.

The invention also provides a mouse whose cells contain the gene for human preproinsulin, proinsulin or insulin and which is capable of producing progeny mice carrying the gene. The invention also provides a mouse whose cells contain the gene for human preproinsulin, proinsulin or insulin and which is capable of producing progeny mice carrying the gene, and wherein the gene is stably expressed.

The invention further provides a method for evaluating the pharmacokinetic effect, therapeutic value, or medical significance of an agent on the expression or level of a heterologous protein which comprises:

(a) providing the agent to a transgenic mammal, the mammal containing the gene for the heterologous protein; and
(b) examining the effect, value or significance of the agent on the expression or level of the heterologous protein, by monitoring the expression or level in the mammal.

The invention also provides a method for evaluating the pharmacokinetic effect, therapeutic value, or medical significance of an agent, on the expression or level of human insulin which comprises:

(a) providing the agent to a mouse whose cells contain and stably express the gene for human preproinsulin, proinsulin or insulin; and
(b) examining the effect, value or significance of the agent on the expression or level of the human insulin by monitoring its expression or level in the mouse.

The invention also provides a transgenic mouse of strain B6C3F1, wherein the transgenic mouse is capable of stably expressing human insulin in a naturally regulated manner. A human C-peptide radioimmunoassay kit (Behringwerke AG, Germany) was used to detect expression of the human insulin gene in this mouse and its offspring. The assay is specific for human C-peptide, showing little or no cross-reactivity with mouse C-peptide. Using this assay, several hundred transgenic mice have been analyzed under a variety of physiological circumstances and shown to produce human C-peptide, thus indicating the expression of human insulin hormone in these mice.

Normal glucose homeostasis wags found to be preserved in these mice, indicating that the expression of the human insulin gene was being appropriately regulated. The level of human insulin in the transgenic mice indicated that insulin expression was under the same regulation and control as either human insulin in humans or murine insulin in mice.

The invention is significant and useful in that it provides an animal model to test for effectors of human insulin hormone in a non-human animal.

DESCRIPTION OF THE PREFERRED EMBODIMENTS

Figure 1A:
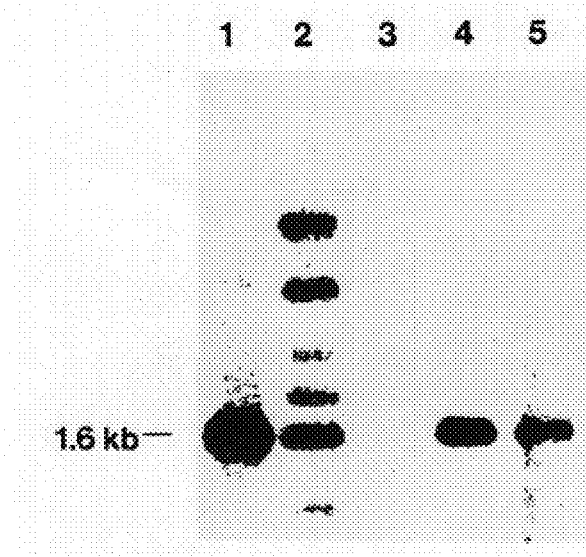
FIG. 1A shows shows the presence of human insulin gene sequences within the chromosomal DNA of the transgenic mouse.

Insulin is a polypeptide hormone that plays the predominant physiologic role in the regulation of fuel homeostasis in an organism. It is synthesized by the beta cells of the Islets of Langerhans (hereinafter described as "Islet cells") of the pancreas. Circulating insulin levels are regulated by several small molecules, notably glucose, amino acids, fatty acids, and certain pharmacologic agents. Insulin consists of two polypeptide chains (A and B, linked by disulfide bonds) that are derived from the proteolytic cleavage of proinsulin, generating equimolar amounts of the mature insulin and a connecting peptide (C-peptide). Proinsulin is produced as a precursor known as preproinsulin. Preproinsulin is processed by the cell into proinsulin which is then excreted from the cell as the mature hormone, insulin. Thus, insulin hormone expression or level may be assayed by measuring either preproinsulin, proinsulin, insulin, A-peptide, B-peptide or, preferably C-peptide, expression or level.

The term "F1," as used herein, refers to the first generation descendants of a mouse (i.e., its "sons and daughters"). The term "F2," as used herein, refers to the second generation decendants of a mouse (i.e., its "grandchildren").

The term "human insulin" refers not only to natural insulin, but also to any analogue thereof. Examples of such analogues are: the product of a human insulin gene which contains a mutation rendering the insulin thereby produced to be functionally impaired, or a naturally occurring human protein which is structurally or functionally similar to normal human insulin, or a novel insulin hormone which results from the in vitro or in vivo mutagenization or modification of the human insulin gene. The term, "human insulin," further refers to variant forms of human insulin. A variant form of human insulin, is a molecule structurally or functionally similar to human insulin which arises natrually or through disease and is present in a subpopulation of the total population.

The term "heterologous protein" refers to a protein which is not normally produced by a particular species. Human insulin, rabbit B-globin are examples of heterologous proteins which may be produced in a mouse. The characteristic of transgenic mammals is that they contain the genes for heterologous proteins, and thus have the capacity to produce heterologous proteins.

The term "cloned gene" refers to a DNA sequence of interest, which has been isolated, and is to be injected into the fertilized egg of a mouse, so as to produce a transgenic mouse which contains the cloned gene sequences.

As used herein, the terms "gene," "DNA sequence" or "genetic sequences" are synonymous, and refer to DNA including any introns or exons which are naturally associated with that DNA. An example of a gene is the DNA which encodes human preproinsulin and the untranslated and intervening sequences which are associated with this DNA sequence (Bell, G. et al., Nature 284:26–31 (1980)). One genetic sequence is said to be derived from a second genetic sequence if it is either an exact copy of the second genetic sequence or if it results from an alteration (i.e. mutation, insertion, or deletion) of the second sequence. A genetic sequence is said to be "expressed" if the gene is transcribed into RNA and the RNA is translated into protein.

The cloned gene, or a fragment of the cloned gene is produced and purified by any of several methods well known to the art. Thus, the cloned gene can be produced synthetically, or by treating mRNA derived from the transcription of the gene with a reverse transcriptase so as to produce a cDNA version of the gene, or by the direct isolation of the gene from a genomic bank or from other sources.

Regardless of how the cloned gene is isolated, it is amplified, and purified away from any other potentially contaminating molecules. Any DNA sequence, such as the human proinsulin gene, a DNA sequence which encodes human insulin, or the gene for human preproinsulin, preferably DNA of plasmid pgHI 12.5 which contains the human preproinsulin gene (Bell, G. et al.), may be used. The sequence of insulin, preproinsulin, and proinsulin is disclosed by Bell, G. et al.

Fertilized mouse eggs for microinjection are recovered in cumulus from the oviducts of female mice that have been mated several hours earlier. Although, fertilized mouse eggs of females from mouse strains C57BL/6J, SJL/Wt, C3H, or C57/SJL may be used, it is preferable to use fertilized mouse eggs from oviducts of C57/C3H F1 females that have mated with F1 males. Fertilized eggs at the pronuclear stage (i.e. the stage at which the male and female pronuclei are separated and distinguishable from each other within the cytoplasm) are collected from the oviducts of the pregnant (C57/C3H) F1 females. The isolated fertilized eggs are incubated at 37° C. in M16 culture medium (Whittingham, D. G., J. Reprod. Fertil. Suppl., 14: 7–21 (1971) and stored for 2–4 hours until micromanipulation. Manipulation of the pipets for holding the fertilized egg to allow the injection of cloned DNA is accomplished by using Leitz micromanipulators and paraffin oil-filled Hamilton syringes. The insulin DNA source to be injected into these embryos should be in 0.5 mM Tris (pH=8) 0.5 mM EDTA. A small drop of culture medium with five or six fertilized eggs is placed on a microscope slide and covered with paraffin oil. Between 2 and 20 pl, but preferably 5 pl of either purified insulin gene fragment or a covalently closed plasmid containing the insulin gene sequence is drawn into the injection pipet which is then moved adjacent to the drop containing the fertilized eggs. A fertilized egg is positioned onto the holding pipet so that the male pronucleus is in juxtaposition to the injection pipet for subsequent injection of the insulin gene solution into the pronucleus. An effective number of copies of the insulin gene sequence, between 600 and 20,000 but preferably 1,000 copies of the insulin gene sequence is injected into each fertilized egg. 60–100 eggs are injected per hour.

After microinjection into all the pronuclei, the fertilized eggs are removed from the drop of medium on the microscope slide and placed in culture tubes for preimplantation development according to the method of Wagner, T. E. et al. After 4 hours of culture at 37° in M16 buffer 1 or 2 fertilized eggs are transplanted into the uteri of one day pseudopregnant ICR foster mothers and carried to term. Pseudopregnant mice are obtained by mating female mice with vasectomized males, as described by Hoppe, P. et al., *Biol. Reprod.* 8:420–426 (1973). Between 10–30 percent of the newborn mammals born to these foster mothers will be transgenic (i.e., will contain within their chromosomes integrated sequences of the cloned gene).

The presence of these integrated sequences is detected by means known in the art and appropriate to the detection of the specific cloned gene. Thus, to detect a gene which does or does not express a polypeptide product, a Southern hybridization analysis is performed. Such techniques, as well as those required for recombinant DNA manipulations, are described in Maniatis, T. et al., *Molecular Cloning: A Laboratory Manual*, Cold Spring Harbor Laboratory, New York, 1982, hereinafter incorporated by reference. Cloned genes, whose presence is expected to be detectable by the production of a polypeptide, such as insulin, may be detected by means which are capable of distinguishing the product of the cloned gene from any endogenous gene product (as, for example, being able to distinguish human insulin from murine insulin), such as radioimmunoassay, enzyme assay, or by other means well known in the art.

Although any suitable means may be used to detect the expression of the cloned gene in the transgenic mouse, it is preferable to use a radioimmune assay, such as the human C-peptide radioimmunoassay kit (commercially available from Behringwerke AG, Germany) which is specific for human C-peptide, showing little or no cross-reactivity with mouse C-peptide, and therefore appropriate to distinguish expression of human insulin from endogenous mouse insulin.

Once a transgenic mouse has been identified, the stable maintenance and transmission of the integrated cloned gene is then confirmed by classical Mendelian experiments as are well known in the art of genetics. A mouse is said to be derived from another mouse if the mice are genetically indistinguishable or if one of the mice is a descendant of the other. A transgenic mouse is said to stably contain a cloned gene sequence, or to stably express a gene product of a cloned gene, if some of the F1 or F2 offspring of the transgenic mouse contain the cloned gene sequence or express the cloned gene product (respectively), in a manner which is either substantially similar to that of the transgenic mouse, or which is substantially distinguishable from that of a non-transgenic mammal.

Typically, it is desirable that the cloned human insulin gene be expressed only in certain tissues, which correspond to those tissues in which the cloned human insulin gene is naturally expressed in its natural host organism. In order to demonstrate tissue specificity, it is sufficient to analyze portions of various tissue from the transgenic mouse to determine whether these tissues express the cloned gene product. Thus, protein derived from various tissue can be assayed by radioimmunoassay or by other means for the presence of the cloned gene product. Alternatively, RNA may be prepared from several tissues and hybridized to a $^{32}P$ or other radiolabeled (or biotinylated) nicktranslated human insulin cDNA probe by means known in the art (Maniatis, T. et al.).

The expression of the cloned human insulin gene sequences will, preferably, be "naturally regulated" by the same mechanisms in a transgenic mouse as it was in its natural host human.

The term "naturally regulated" means that the gene is regulated in a physiologically appropriate mannner. Hence, the gene's expression may not be constituitive, but will vary in response to the requirements, activities and effectors of the trangenic mouse. "Natural regulation" requires that the cloned human insulin gene may not be expressed in all tissues and organs of the mouse, but only in those tissues and organs in which the cloned insulin gene was expressed in its natural host. Further, such "natural regulation" requires that the insulin gene sequences, their corresponding mRNA transcripts, and the proteins produced from these transcripts, be "naturally processed." The term "naturally processed" involves such steps as mRNA transcription, splicing, and proteolytic cleavage of protein precursor molecules (such as preproinsulin or proinsulin). Additionally, "natural regulation" will cause a level of insulin gene expression which is within a normally encountered physiological range rather than an abnormal range. The physiologically normal range of insulin concentration in a mouse is 0–100 uU/ml. Thus, for example, the expression of the human preproinsulin gene in a transgenic mouse would be "naturally regulated" if (1) expression occurred only in the Islet cells of the pancreas of the mouse, (2) the preproinsulin produced was naturally processed to proinsulin and the naturally produced proinsulin was further naturally processed to insulin which was naturally secreted into the circulatory system of the mouse, (3) the amount of preproinsulin, proinsulin and insulin produced was within a normal physiological range, (4) the presence of affectors of insulin expression (such as glucose or amino acids) will cause the amount and concentration of human preproinsulin, proinsulin and insulin to vary in a manner which is essentially identical to that in which murine preproinsulin, proinsulin and insulin would vary in the mouse or human preproinsulin, proinsulin or insulin would vary in humans.

Transgenic mice which produce the human insulin hormone are especially useful to the pharmaceutical industry. Such mice provide, for the first time, an in vivo non-human animal model for evaluating the effect of a drug or other agent on human insulin levels. Currently, any effort to make such an evaluation requires volunteers or patients. The ethical constraints which are encountered in research involving human subjects greatly limits the nature and scope of investigations of human insulin-therapeutic agent interactions.

In an exactly analogous manner one could determine the pharmacological effects, therapeutic value, and medical significance of an agent by administering the agent to any transgenic mammal and evaluating the potential effect of the agent on the expression and level of any heterologous protein produced by the transgenic mammal. Thus, for example, if one had produced a transgenic mammal which produced heterologous protein primarily in its choroid plexus (as did Swift, G. M. et al.) then one could assess the effects of agents on the choroid plexus, or the ability of agents to enter the choroid plexus by studying the expression of the heterologous protein. Hence, the present invention teaches more than the use of transgenic mammals to study insulin expression; the present inventions discloses the utility of transgenic mammals, and especially transgenic mice, in the general study of pharmacology and medicine.

The ability to produce a transgenic mouse which expresses an analogue of human insulin permits investigations of the structure and function of the insulin hormone. Previously, such studies were difficult to perform because of the rarity of individuals expressing such analogues, and because the amount of hormone produced in such subjects or patients is extremely limited. In contrast, the ability to produce transgenic mice which express analogues of human insulin enables the purification and characterization of such analogues. The amount of the natural analogues available would be limited solely by the size of the colony of mice used in the investigation. Moreover, the ability to manipulate insulin gene sequences in vitro and to introduce those sequences back into a mouse, thus producing a transgenic mouse which expresses a novel insulin hormone provides an extraordinary tool to investigate the relationship between hormones structure and function.

E. coli strain containing plasmid pgHI 12.5 is described by Bell, G. I. et al.

Having now generally described this invention, the same will be better understood by reference to certain specific examples which are included herein for purposes of illustration only and are not intended to be limiting of the invention, unless specified.

EXAMPLE I

Preparation of the Cloned Insulin Fragment

Insulin mRNA was isolated from pancreatic cells and used to produce a cDNA probe (Lawn, R. M. et al.; Bell, G. I. et al.). A human gene library in bacteriophage lambda Charon 4A was incubated in the presence of the cDNA probe. Two out of approximately $10^6$ phages hybridized with the probe. One of these clones contained a 12.5 kb EcoRI fragment which contained the complete nucleotide sequence of the cloned human preproinsulin gene. This 12.5 kb fragment was subcloned into the plasmid pBR322, and designated pgHI 12.5 introduced into the bacterium E. coli, strain DK1 and thereby amplified. After amplification the 12.5 kb fragment was excised from the plasmid and purified. Approximately 1,000 copies of this fragment were microinjected into the male pronucleus of single-cell mouse embryos, which were then transferred to pseudopregnant foster mothers for gestation. Of 46 mice born after one series of injections, three (approximately 7%) contained human insulin gene sequences as detected by Southern hybridization analysis. One mouse, a male, was found to contain from 5 to 10 copies of the human insulin gene fragment per haploid genome, and was characterized further. This mouse was bred to generate a colony of several hundred offspring, and the human insulin gene sequences were found to be transmitted in a Mendelian fashion, with approximately 50% of both the F1 and F2 offspring inheriting the injected DNA fragment. Mouse No. 16 which was found to be a transgenic, human insulin producing mouse was bred with a female mouse of strain B6C3F1, to generate progeny mice. By assaying for human insulin production in these mice and selectively mating human insulin-producing siblings, a colony of homozygous, human-insulin producing mice was obtained. The homozygous human-insulin producing mice were designated B6C3F1/huming.

The characterization of the transgenic mice is shown in FIG. 1A. Chromosomal DNA from several mice were tested to determine whether the mice carried human insulin DNA sequences. DNA samples were digested with Pvu II and analyzed by a Southern hybridization analysis (Maniatis, T. et al.) using a radio-labeled 1594 bp Pvu II fragment (contained within the 12.5 kb human insulin DNA fragment) as a probe. Lanes 1, 2 and 5 show hybridization between the probe and genomic sequences of transgenic mice. Lane 3 shows the absence of hybridization between the probe and genomic sequences of a non-transgenic sibling mouse. Lane 4 shows the hybridization between the probe and genomic DNA of a human control. For the Southern blot analysis, 8 ug of total genomic DNA for each mouse were digested with Pvu II, subjected to electrophoresis on a 0.9% agarose gel, and transferred to nitrocellulose. The filter was then prehybridized overnight, hybridized to a $^{32}$P-labeled genomic human insulin probe, washed, and exposed to x-ray film. The genomic insulin probe was a fragment that extends from a Bgl II site at −169 with respect to the transcriptional start site of the human insulin gene to an Ava I site at +644. In addition to promoter sequences, this fragment contained the first intervening sequence, the first exon (including sequences encoding the signal peptide, B-peptide, and a portion of the C-peptide), and a portion of the second intervening sequence. The genomic human insulin probe showed limited cross hybridization with the endogenous mouse insulin genes.

EXAMPLE II

Confirming the Expression of the Cloned Human Insulin Hormone Gene in the Mouse

Figure 1B:
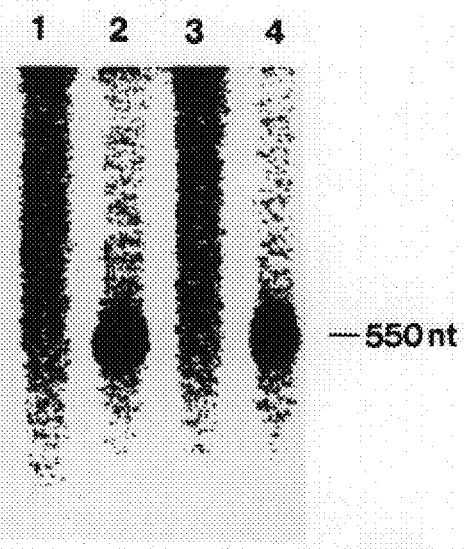
FIG. 1B shows the presence of human and mouse insulin mRNAs in tissues of transgenic and control mice.

The presence of DNA which contains human insulin gene sequences was detected in the mouse B6C3F1/Huming through the use of Southern hybridization analysis. To determine the tissue specificity of human insulin gene expression in the transgenic mice, both RNA analyses and pancreatic islet function studies were performed. Total RNA from several tissues was prepared from transgenic mice and non-transgenic siblings. This RNA was separated by electrophoresis on 1.2% agarose-formaldehyde gels, transferred to nitrocellulose, and hybridized to a $^{32}$P-labeled nick-translated human insulin cDNA probe. The results of this experiment are shown in FIG. 1B (lane 1, RNA from liver of nontransgenic mouse; lane 2, RNA from pancreas of nontransgenic mouse; lane 3, RNA from liver of transgenic mouse; lane 4, RNA from pancreas of transgenic mouse) although pancreatic RNA from both transgenic and control mice hybridized to the human insulin cDNA probe, RNAs from transgenic and control liver, spleen, brain, kidney, heart, intestine, lung, and muscle showed no hybridization. Neither the mouse insulin cDNA, nor gene sequences, have been determined, but since the coding regions of the rat and human insulin mRNAs share 81% sequence homology (Bell, G. I. et al.), it was expected that both transgenic and control pancreatic RNAs would hybridize to the human probe. These results indicated that the human insulin gene was expressed only in the pancreas of the transgenic mouse of strain B6C3F1/Huming, and not in any of the other tissues tested. Since no transgenic tissues other than the pancreas were found to express detectable levels of insulin RNA, insulin expression in both transgenic and control pancreas was studied to determine if the transgenic pancreas was a site of human insulin expression. Pancreatic islets from six transgenic and six control mice were isolated by collagenase digestion (Lacy et al., *Diabetes* 16:35–39 (1967)) and cultured in groups of approximately 80–100 Islet cells/tissue culture well. The following day, aliquots of media were taken, and human C-peptide levels were measured. The samples from the tissue culture wells containing Islets cells from the pancreas of transgenic mice contained 250–650 ng/ml of human C-peptide, but the tissue culture wells containing Islet cells from the pancreas of control mice contained no detectable human C-peptide. The cultured transgenic Islet cells continued to express human C-peptide for several days. From these experiments, the major site of human insulin expression in transgenic mice of strain B6C3F1/Huming has been determined to be the endocrine pancreas.

Transgenic and control pancreases were immunoperoxidase stained using a guinea pig anti-porcine insulin antibody and a goat anti-human C-peptide antibody. The anti-porcine insulin antibody cross-reacts with both human and mouse insulin, and Islets cells from both transgenic and control mice are stained. The size, distribution, and number of islets were essentially the same in both transgenic and control mice. Importantly, only the Islet cells of transgenic mice and not the islet cells of control mice were stained using an anti-human C-peptide antibody. This reflects the fact that the anti-human C-peptide antibody showed little or no cross-reactivity with mouse C-peptide. The immunohistochemistry data were consistent with the Northern analysis and islet function studies presented above, and demonstrated that the islet cells of transgenic mice of strain B6C3F1/Huming were specifically expressing human insulin.

EXAMPLE III

Figure 2:
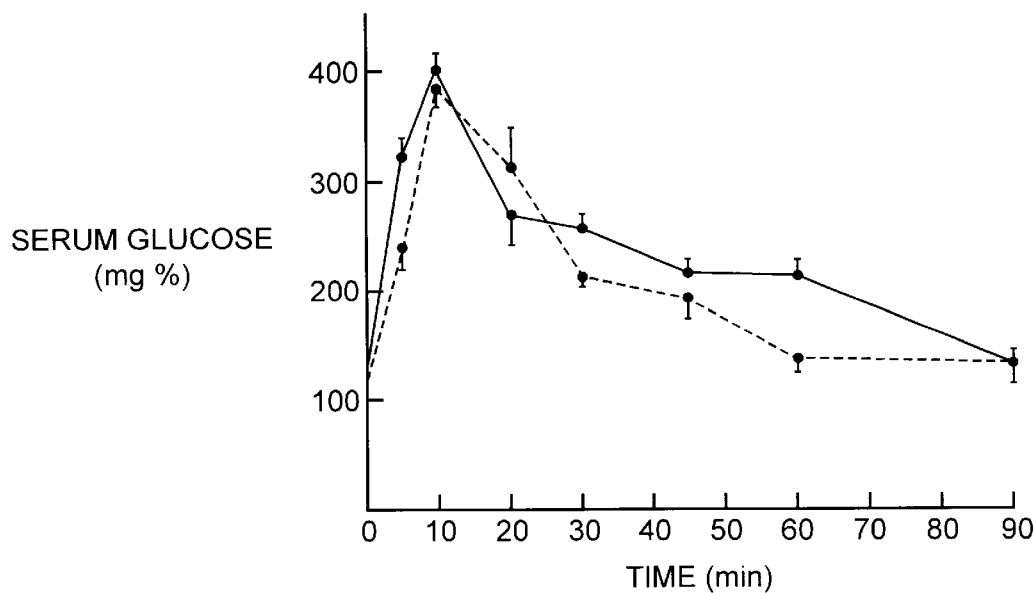
FIG. 2 shows the serum glucose levels in transgenic and control mice following an intraperitoneal glucose injection.
Figure 3:
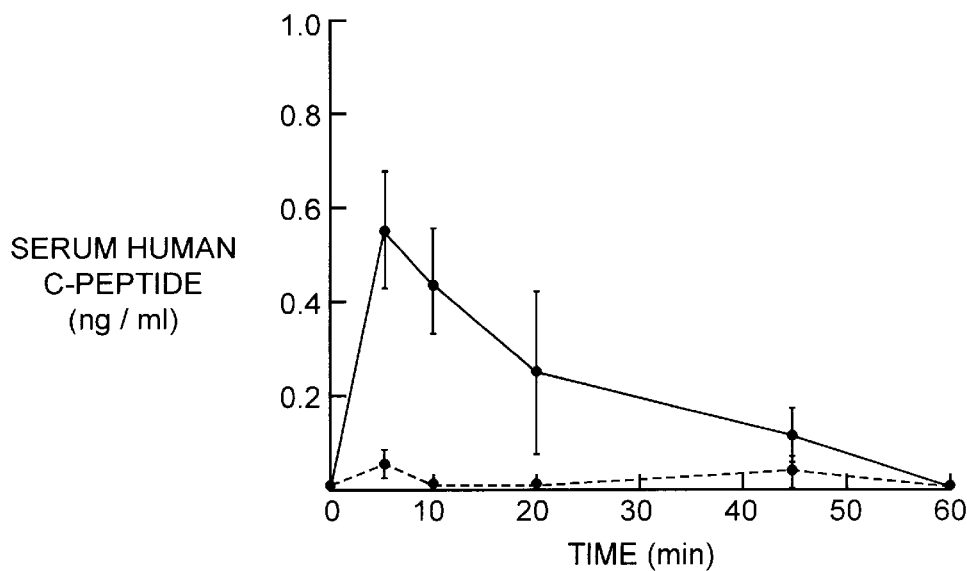
FIG. 3 shows human C-peptide levels during an intravenous amino acid tolerance test on transgenic and control mice.

Studies of Physiological Regulation of Glucose and Human Insulin Levels in the Transgenic Mice Glucose and human C-peptide levels in transgenic mice of strain B6C3F1/Huming were studied under a variety of physiological conditions to determine if normal glucose homeostasis was being preserved, and if the expression of the human insulin gene was being regulated appropriately in these mice. To study blood glucose regulation, glucose tolerance tests were performed. Transgenic offspring of mouse #16 and nontransgenic siblings were fasted overnight, given an intraperitoneal injection of glucose (1 mg/gm body weight), and bled at various times after injection to determine serum glucose levels. The glucose tolerance curve from the transgenic mice is similar to that from the control mice (FIG. 2). (Each mouse was arbitrarily chosen for serum sampling at one of the following times after infection: 5, 10, 20, 30, 45, 60, or 90 minutes, shown by solid line. Four mice did not receive glucose and were bled to determine fasting serum glucose levels (dashed line). The human C-peptide levels in the sera of these mice were measured using a commerically available kit (Behringwerke AG, Germany) under the conditions recommended by the manufacturer. Serum human C-peptide levels of these transgenic mice are shown in FIG. 3 by a solid line; those of control mice are shown by a dashed line). Of particular importance is that the fasting and maximally stimulated glucose levels as well the kinetics of the return to basal glucose levels are similar for the transgenic and control animals. In addition, intravenous administration of glucagon increased serum glucose levels by approximately 50% within 15 minutes in both transgenic anc control mice. Taken together, these results strongly suggest that serum glucose levels are appropriately modulated in the transgenic mice. The weights of the transgenic mice, growth rates, feeding behavoir, reproductive capability, and longevity appear normal.

Figure 4:
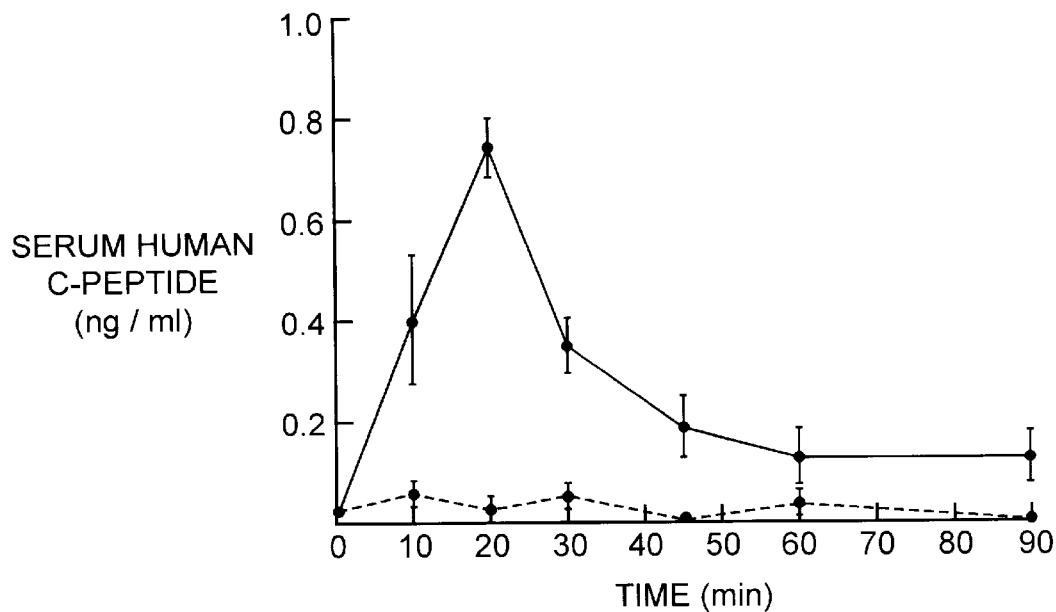
FIG. 4 shows human C-peptide levels during an intraperitoneal glucose tolerance test on transgenic and control mice.

The role of human insulin in the regulation of blood glucose levels in transgenic mice was investigated by performing a glucose tolerance test on transgenic and control mice (FIG. 4). No human C-peptide was detectable in the sera of fasting transgenic mice. Within 10 minutes of intraperitoneal administration of glucose, however, human C-peptide appears in the serum, and peak levels are attained in approximately 20 minutes. By 45 minutes post-glucose injection, human C-peptide levels fell to values approaching the pre-stimulation or basal level. This pattern of human C-peptide expression correlated closely with the glucose tolerance curves previously described, and indicated that, in transgenic mice of strain B6C3F1/Huming the serum human insulin levels were appropriately regulated by glucose. In addition, these data were similar to glucose tolerance results previously reported for both mice and humans (Larkins, *Diabetes* 22:251–255 (1973); Rubenstein, in *Endocrinology*, Vol II (Eds. DeGroot et al.) 951–957 (Grune and Stratton, pub. 1979). The control mice did not express any detectable human C-peptide, indicating that the human gene must be the source of the human C-peptide in the transgenic mice.

Figure 5:
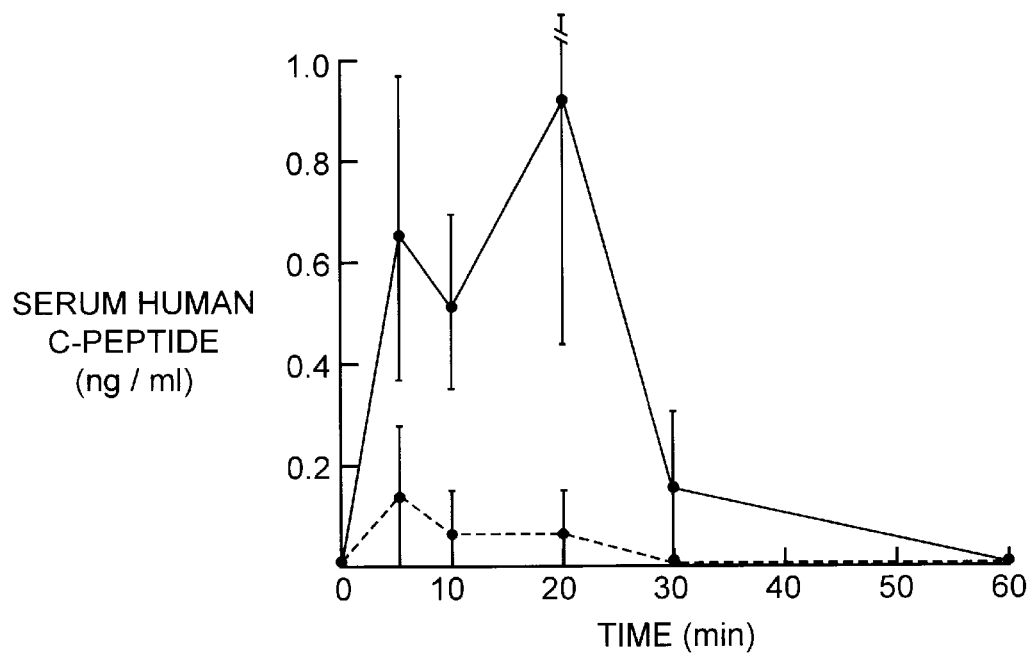
FIG. 5 shows human C-peptide levels during an intravenous tolbutamide infusion test on transgenic and control mice.

Insulin is regulated by several other factors, including amino acids and certain pharmacologic agents. An intravenous amino acid infusion test was performed on fasting transgenic and control mice and human C-peptide levels in the serum were determined. Peak human C-peptide levels were seen within 5 minutes of amino acid infusion and gradually declined over the next 40 minutes. Transgenic mice of strain B6C3F1/Huming and control mice were fasted overnight, infused with 0.5 mg arginine and 0.5 mg leucine, and bled at the indicated times for human C-peptide determination. The results of this experiment are shown in FIG. 4. Each time point represents the average of values from four animals. The solid lines indicate data from transgenic mice; the dashed lines indicate data from control mice. Similarly, serum human C-peptide levels respond to tolbutamide, a sulfonylurea derivative known to promote insulin release (Ganda, O. P. et al., *Diabetes* 24:354–361 (1975)). Transgenic and control mice were fasted overnight, infused with 0.5 mg of tolbutamide (The Upjohn Company, Michigan), and bled at the indicated times for human C-peptide determination (FIG. 5). Each time point represents the average of values from two animals. Data from transgenic mice are shown by solid lines; data from control mice are shown by dashed lines.

Tolbutamide has been used clinically to diagnose insulinomas because in normal subjects, serum insulin (or C-peptide) levels rapidly return to normal from their tolbutamide induced peak, but in insulinoma patients, elevated insulin levels persist (Fajans, S. S. et al., *J. Lab. Clin. Med.* 54:811 (1959)). Within 20 minutes of intravenous tolbutamide administration, serum human C-peptide levels peaked, followed by a rapid decrease over the next 10 minutes.

The fact that transgenic mice of strain B6C3F1/Huming quickly regained basal serum human C-peptide levels supports the conclusion that their insulin expression was tightly regulated. The tolbutamide results presented above have significant implications for insulin pharmacologists. Drugs that are thought to affect human insulin synthesis, secretion, action or clearance can now be tested in an in vivo animal system. The in vivo effects of various pharmacological agents on human gene expression and protein function can now be evaluated in a non-human setting.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the amended claims.

What is claimed is:

1. A mouse whose genome comprises a genomic DNA fragment wherein the DNA fragment comprises a coding sequence for human preproinsulin, wherein said mouse can be bred to produce progeny mice whose genomes comprise said genomic DNA fragment, and wherein said genomic DNA fragment:

a) is expressed in Islet cells of the pancreas of said mouse or said progeny;

b) encodes human preproinsulin, which is processed to proinsulin and then to insulin which is secreted into the circulatory system of said mouse or said progeny;

c) is expressed as insulin within the normal physiologic range for a mouse in said mouse or said progeny; and d) is expressed as insulin in response to affectors of insulin expression which result in regulated expression of insulin.

2. The mouse of claim 1, which is strain B6C3F1/Huming.

3. Progeny of the mouse according to claim 1 wherein said progeny have inherited said genomic DNA fragment and wherein said genomic DNA fragment:

a) is expressed in the Islet cells of the pancreas of said mouse or said progeny;

b) encodes human preproinsulin which is processed to proinsulin and then to insulin which is secreted into the circulatory system of said mouse or said progeny;

c) is expressed as insulin within the normal physiologic range for a mouse in said mouse or said progeny; and d) is expressed as insulin in response to affectors which regulate insulin expression in humans.

4. The progeny of claim 3 wherein said progeny are homozygous for said genomic DNA fragment.

5. The progeny of claim 3 wherein said progeny are heterozygous for said genomic DNA fragment.

6. The progeny of claim 5 wherein said genomic DNA fragment is inherited from a male parent.

7. The progeny of claim 5 wherein said genomic DNA fragment is inherited from a female parent.

8. A transgenic mouse which expresses a genomic DNA fragment which comprises a coding sequence for human preproinsulin, wherein said transgenic mouse can be bred to produce progeny mice whose genomes comprise said genomic DNA fragment and further wherein said human preproinsulin, proinsulin or insulin is only expressed in the Islet cells of the pancreas of said progeny mice.

9. The mouse of claim 8 wherein the genomic DNA encoding human preproinsulin is a 12.5 kb genomic DNA fragment.

10. A method for obtaining a target mouse whose genome comprises a genomic DNA fragment wherein the DNA fragment comprises a coding sequence for human preproinsulin, wherein said mouse can be bred to produce progeny mice whose genomes comprise said genomic DNA fragment, said method comprising the steps of:

a) insolating a fertilized egg from a first female mouse;

b) transferring a genomic DNA fragment which comprises a coding sequence for human preproinsulin into said fertilized egg;

c) transferring said fertilized egg containing said genomic DNA fragment to the uterus of a pseudopregnant second female mouse; and d) maintaining said second female mouse such that:
(i) said second female mouse becomes pregnant with an embryo derived from said fertilized egg containing said genomic DNA fragment;
(ii) said embryo develops into said target mouse; and
(iii) said target mouse is viably born from said second female mouse;

wherein the genome of said target mouse comprises the genomic DNA fragment of b) and wherein said mouse can be bred to produce progeny mice whose genomes comprise said genomic DNA fragment, and further wherein said genomic DNA fragment:

(i) is expressed in the Islet cells of the pancreas of said target mouse or said progeny;

(ii) encodes human preproinsulin which is processed to proinsulin and then to insulin, which is secreted into the circulatory system of said target mouse or said progeny;

(iii) is expressed as insulin within the normal physiologic range for a mouse in said target mouse or said progeny; and (iv) is expressed as insulin in response to affectors of human insulin expression which results in regulated expression of insulin.

11. The method of claim 10 wherein the DNA fragment is a 12.5 kb genomic DNA fragment.

12. The method of claim 11 wherein the 12.5 kb genomic DNA fragment is a 12.5 kb EcoRI genomic DNA fragment.

13. A method for obtaining a target mouse whose genome comprises a genomic DNA fragment wherein the DNA fragment comprises a coding sequence for human preproinsulin wherein the human preproinsulin is expressed as insulin in the target mouse in response to affectors of human insulin expression which results in regulated expression of insulin and wherein said mouse can be bred to produce progeny mice whose genomes comprise said genomic DNA fragment, said method comprising:

a) isolating a fertilized egg from a first female mouse;

b) transferring a genomic DNA fragment which comprises a coding sequence for a human preproinsulin into said fertilized egg;

c) transferring said fertilized egg containing said genomic DNA fragment to the uterus of a pseudopregnant second female mouse; and d) maintaining said second female mouse such that:
(i) said second female becomes pregnant with an embryo derived from said fertilized egg containing said genomic DNA fragment,
(ii) said embryo develops into said target mouse, and
(iii) said target mouse is viably born.

14. A method for obtaining a mouse according to claim 1 comprising:

a) isolating fertilized egg from a first female mouse;

b) transferring said genomic DNA fragment into said fertilized egg;

c) transferring said fertilized egg containing said genomic DNA fragment to the uterus of a pseudopregnant second female mouse; and d) maintaining said second female mouse such that:
(i) said second female mouse becomes pregnant with an embryo derived from said fertilized egg containing said genomic DNA fragment,
(ii) said embryo develops into said mouse, and
(iii) said mouse is viably born from said second female mouse;

wherein said mouse's genome comprises said DNA fragment and said mouse can be bred to produce progeny mice whose genomes comprise said DNA fragment.

15. A method for obtaining a target mouse whose genome comprises a genomic DNA fragment wherein the DNA fragment comprises a coding sequence for a human preproinsulin, wherein said target mouse can be bred to produce progeny mice whose genomes comprise said DNA fragment, comprising:

a) insolating a fertilized egg from a first female mouse;
b) transferring said genomic DNA fragment into said fertilized egg;
c) transferring said fertilized egg containing said genomic DNA fragment to the uterus of a pseudopregnant second female mouse; and
d) maintaining said second female mouse such that:
   (i) said second female mouse becomes pregnant with an embryo derived from said fertilized egg containing said genomic DNA fragment,
   (ii) said embryo develops into said target mouse, and
   (iii) said target mouse is viably born from said second female mouse, wherein in the target mouse, the human preproinsulin is expressed in the Islet cells of the pancreas.

16. The method of claim 15 wherein the genomic DNA fragment is a 12.5 kb genomic DNA fragment.

17. The method of claim 16 wherein the genomic DNA fragment is a 12.5 EcoRI genomic DNA fragment.

18. A method for evaluating the pharmacokinetic effect, potential therapeutic value, or potential medical significance of an agent, on the expression or level of human insulin which comprises:
a) providing said agent to the mouse of claim 1; and
b) examining the pharmacokinetic effect, potential value or potential significance of said agent on the expression or level of said human insulin, by monitoring said expression or level in said mouse.

19. The method of claim 18, wherein said mouse is derived from strain B6C3F1/Huming.

20. A method for evaluating in a non-human transgenic mammal the pharmacokinetic effect, potential therapeutic value, or potential medical significance of an agent on the expression or level of a human protein encoded by a transgene, wherein the transgene comprises a genomic DNA fragment which comprises a coding sequence for the human protein, wherein said human protein is expressed in the transgenic non-human mammal in response to affectors of expression of the human protein which result in regulated expression of the human protein in humans, said method comprising the steps of:
a) providing said agent to said transgenic non-human mammal whose genome comprises said transgene, wherein said mammal expresses the human protein and can be bred to produce a progeny mammals whose genomes comprise said transgene and whose cells express the human protein in response to affectors which regulate expression of said protein in humans; and
b) evaluating the pharmacokinetic effect, potential therapeutic value, or potential medical significance of said agent on the expression or level of said human protein, by monitoring said expression or level in said non-human transgenic mammal.

21. The method of claim 20 in which the non-human transgenic mammal is a transgenic rodent.

22. The method of claim 21 wherein the human protein is a hormone.

23. The method of claim 20, wherein said transgenic mammal is a transgenic mouse.

24. The method of claim 20 wherein the human protein is a hormone.

25. A method for evaluating in a transgenic rodent the pharmacokinetic effect, potential therapeutic value, or potential medical significance of an agent on the expression of a human protein encoded by a genomic DNA fragment which comprises a coding sequence for said human protein, said method comprising the steps of:
a) providing an agent to said transgenic rodent whose genome comprises said genomic DNA fragment and which expresses said protein in a tissue specific fashion, at physiologically normal levels, in response to affectors which regulate expression of said protein in humans, and wherein said transgenic rodent can be bred to produce progeny whose genome also comprises said genomic DNA fragment and which is phenotypically similar to the parent; and
b) evaluating the pharmacokinetic effect, potential therapeutic value, or potential medical significance of said agent on the expression level of said human protein, by monitoring expression or protein production in said transgenic rodent.

26. The method of claim 25 wherein the rodent is a mouse.

* * * * *